(12) United States Patent
Uematsu et al.

(10) Patent No.: US 11,571,698 B2
(45) Date of Patent: Feb. 7, 2023

(54) BACTERIAL TEST PLATE HAVING ANTIBACTERIAL AGENT INTRODUCED THEREINTO, AND TRANSPARENT PLATE

(71) Applicant: HITACHI HIGH-TECH CORPORATION, Tokyo (JP)

(72) Inventors: Chihiro Uematsu, Tokyo (JP); Yuichi Uchiho, Tokyo (JP); Akira Masuya, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 377 days.

(21) Appl. No.: 16/769,841

(22) PCT Filed: Nov. 2, 2018

(86) PCT No.: PCT/JP2018/040829
§ 371 (c)(1),
(2) Date: Jun. 4, 2020

(87) PCT Pub. No.: WO2019/116775
PCT Pub. Date: Jun. 20, 2019

(65) Prior Publication Data
US 2020/0391206 A1 Dec. 17, 2020

(30) Foreign Application Priority Data
Dec. 13, 2017 (JP) .............................. JP2017-238971

(51) Int. Cl.
*C12Q 1/00* (2006.01)
*B01L 3/00* (2006.01)
*C12Q 1/18* (2006.01)

(52) U.S. Cl.
CPC .............. *B01L 3/5085* (2013.01); *C12Q 1/18* (2013.01); *B01L 2300/0832* (2013.01)

(58) Field of Classification Search
CPC .................................................... B01L 3/5085
See application file for complete search history.

(56) References Cited

U.S. PATENT DOCUMENTS

| 2007/0037225 A1 | 2/2007 | Metzger et al. |
| 2015/0337352 A1 | 11/2015 | Kwon et al. |
| 2019/0100786 A1 | 4/2019 | Kwon et al. |

FOREIGN PATENT DOCUMENTS

| EP | 3202885 A1 | 8/2017 |
| FR | 1488866 A | 7/1967 |
| JP | 2-501349 A | 5/1990 |
| JP | 2008-523820 A | 7/2008 |
| WO | 1989/002927 A1 | 4/1989 |
| WO | 99/45095 A1 | 9/1999 |
| WO | 2017/183875 A1 | 10/2017 |
| WO | 2018/150414 A1 | 8/2018 |

OTHER PUBLICATIONS

Choi, J. et al, Direct, rapid antimicrobial susceptibility test form positive blood cultures based on microscopic imaging analysis, Sci. Rep., Apr. 25, 2017, vol. 7, art. No. 1148 (pp. 1-13).
Avesar, J. et al, Rapid phenotypic antimicrobial susceptibility testing using nanoliter arrays, Proc. Natl. Acad. Sci. USA, Jun. 26, 2017, vol. 114, No. 29, pp. E5787-E5795.
International Search Report and English Translation, PCT/JP2018/040829 dated Dec. 18, 2018, 3 pgs.
Japanese Office Action dated Oct. 26, 2021 for Japanese Patent Application No. 2017-238971.
Choi et al., A Rapid Antimicrobial Susceptibility Test Based on Single-Cell Morphological Analysis, Science Translational Medicine, vol. 6, Issue 267, Dec. 17, 2014.
Extended European Search Report dated Sep. 1, 2021 for European Patent Application No. 18888161.9.

*Primary Examiner* — Albert M Navarro
(74) *Attorney, Agent, or Firm* — Volpe Koenig

(57) ABSTRACT

Provided is an antibacterial agent-containing dried plate having no cracks on an observation surface (a part of the plate corresponding to an observation visual field of a microscope). According to the present embodiment, an antibacterial agent-introduced plate obtained by introducing an antibacterial agent and performing vacuum drying has a recess at an edge of a well, and a microscopic observation portion, which has a surface substantially parallel to a well bottom surface, near the center of the well. The recess is provided between the microscopic observation portion and a side wall of the well, and is lower in height than the microscopic observation portion. Further, at least the bottom surface of the well and the microscopic observation portion are made of a material having a light-transmitting property in order for optical measurement (FIG. 1).

10 Claims, 8 Drawing Sheets

BACTERIAL TEST PLATE HAVING ANTIBACTERIAL AGENT INTRODUCED THEREINTO, AND TRANSPARENT PLATE

TECHNICAL FIELD

The present disclosure relates to an antibacterial agent-introduced plate used for testing bacteria, fungi, and the like.

BACKGROUND ART

Conventionally, in antimicrobial susceptibility testing for bacteria, bacteria are introduced and cultured in a culture medium containing various antibacterial agents at various concentrations in a culture plate. The culture medium containing about 10 to 20 antibacterial agents at various concentrations is introduced into the culture plate. The bacteria is inoculated therein and is cultured. However, preparation of the culture medium containing the antibacterial agents requires time and effort. For this reason, in many cases, a culture medium containing an antibacterial agent is introduced into a plate in advance, and the frozen plate or dried plate is used.

SUMMARY OF INVENTION

Technical Problem

In antimicrobial susceptibility testing for bacteria and fungi, the turbidity of a culture medium is measured to determine whether or not bacteria have grown. In order to rapidly perform such determination by the turbidity measurement, the growth of each bacterium can be monitored by microscopic observation of the culture medium to determine the growth. In this rapid antimicrobial susceptibility testing, a plate in which a culture medium is to be introduced needs to be optically transparent for microscopic observation of the culture medium.

An antibacterial agent-containing dried plate in which the antibacterial agent has been introduced in advance is often used as a culture container in the antimicrobial susceptibility testing, but there is a problem that resin on a bottom surface of the plate cracks during drying to obstruct the microscopic observation.

Therefore, if the antibacterial agent-containing dried plate, which is often used in the antimicrobial susceptibility testing, is directly applied to the rapid antimicrobial susceptibility testing using the microscopic observation, cracks in the plate, which obstruct the observation of bacteria, are detected. Incidentally, the degree of the cracks of the plate is recognized in the microscopic observation (when observed with a phase contrast microscope or when an image acquired with an optical microscope is contrasted by image processing), and does not affect the normal turbidity measurement.

The present disclosure has been made in view of such a situation, and provides an antibacterial agent-containing dried plate that is free from cracks on an observation surface (a portion of the plate corresponding to an observation visual field of a microscope).

Solution to Problem

In order to solve the above problem, an antibacterial agent-introduced dried plate according to the present disclosure is prepared by introducing a culture medium containing an antibacterial agent into a plate provided with a recess at an edge of a well of the plate into which the antibacterial agent is to be introduced, and then performing vacuum drying, as an example. Depending on a condition of the vacuum drying, the plate may crack when a liquid evaporates. However, if the vacuum drying is performed under such a condition that the liquid gradually evaporates, the liquid remains at the edge of the plate so that cracks are generated only at the edge of the well. As a result, no cracks are generated in a portion where microscopic observation is performed so that the microscopic observation becomes possible. This provides a crack-free antibacterial agent-introduced dried plate.

An antibacterial agent-introduced plate according to the present disclosure is, for example, an antibacterial agent-introduced plate including a plurality of holding portions that hold a culture medium to be used for antimicrobial susceptibility testing, the plurality of holding portions holding dried culture medium and antibacterial agent. Each bottom surface of the plurality of holding portions includes a light-transmitting surface. Further, each of the plurality of holding portions includes a trap portion that traps the culture medium on a part of the bottom surface.

Another characteristic relating to the present disclosure will become apparent from the description of the present specification and the accompanying drawings. Further, aspects of the present disclosure are achieved and realized by elements and combinations of various elements, and the following detailed description and aspects of the appended claims.

It is to be understood that the description in the present specification is merely illustrative and is not intended to limit the scope of the claims or the application by no means.

Advantageous Effects of Invention

According to the present disclosure, the crack-free antibacterial agent-introduced plate is provided so that the time and effort required for preparing a plate in antimicrobial susceptibility testing are reduced. In addition, the rapid test is achieved by using microscopic observation. Further, a culture plate can be observed with a microscope with high accuracy.

DESCRIPTION OF EMBODIMENTS

Figure 1A:
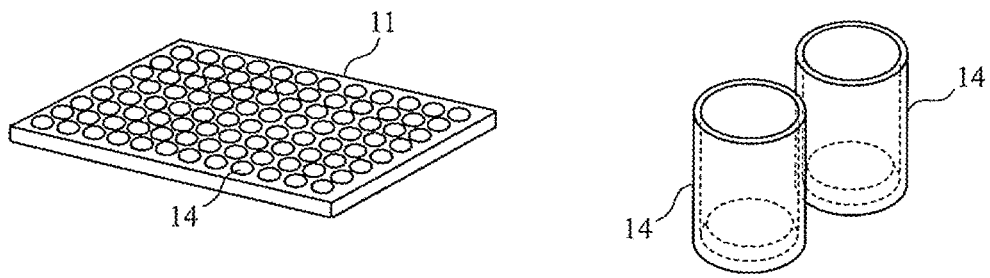
FIGS. 1A-1D are views illustrating a configuration example of an antibacterial agent-introduced plate according to Working Example 1.

Hereinafter, an embodiment and working examples of the present disclosure will be described with reference to the accompanying drawings. In the accompanying drawings, functionally identical elements are sometimes denoted by the same number. Incidentally, the accompanying drawings illustrate specific embodiment and working examples in accordance with the principle of the present disclosure, these are described for the understanding of the present disclosure, and are not used to limit the present disclosure by no means.

The present embodiment is described in sufficient detail for those skilled in the art to carry out the present disclosure. However, other types of implementation and forms can be applied, and it is necessary to understand that changes in configurations and the structures can be made and elements can be variously replaced without departing from the scope and the gist of the technical idea of the present disclosure. Therefore, the following description shall not be interpreted in a manner of being limited thereto.

(1) Embodiment: Overview

When performing antimicrobial susceptibility testing for bacteria and fungi, typically, a culture medium containing various antibacterial agents at various concentrations is introduced into a well such as a microplate, and further, a bacterial suspension is introduced therein to perform culture while keeping a temperature at about 35° C. Whether the bacteria have grown after the culture is determined. Conventionally, whether the bacteria have grown is determined by measuring the turbidity of the culture medium. When the culture medium is observed with a microscope, it is possible to monitor the division of each bacterium, and thus, the determination can be speeded up. However, in an antibacterial agent-introduced plate often used in antimicrobial susceptibility testing, cracks may be generated on a bottom surface of a resin plate when a culture medium containing an antibacterial agent is prepared by vacuum drying. These cracks are almost invisible to the naked eye and do not affect the turbidity measurement, but can be confirmed by microscopic observation. The cracks sometimes hinder the observation of bacteria.

The antibacterial agent-introduced plate of the present disclosure is characterized in that there are no cracks in a microscopic observation region on a bottom surface of the plate.

For example, the antibacterial agent-introduced plate is prepared by introducing a culture medium containing an antibacterial agent into a well of a resin microplate, and then, drying a liquid in the well under vacuum. If a vacuum condition at the time of vacuum drying is, for example, about 50 Pa, drying is rapidly performed since the degree of vacuum is high (there is little air). Thus, when the liquid in the well evaporates, cracks are sometimes generated on the bottom surface of the resin plate. On the other hand, when the condition at the time of vacuum drying is about 1000 Pa, no cracks are generated on the bottom surface of the well, but components of the antibacterial agent or the culture medium remain in the well, and the components are not redissolved even when a liquid is added. In other words, there are problems that the entire bottom surface of the well cracks if the liquid is quickly evaporated, and the components remain without being dissolved (the components are not easily redissolved when water is injected into the plate again) if the liquid is slowly evaporated conversely. Therefore, a trap portion (a portion to hold the culture medium) such as a recess and a protrusion is provided at an edge of the well in the present embodiment. Since the culture medium is an aqueous solution, a liquid level at the edge of the well is slightly higher than that at the center of the well due to a meniscus. When the liquid is slightly evaporated in the well having the recess at the edge in this manner, the liquid in the center of the well is dried and disappears first, and the liquid remains at the edge of the well. Therefore, cracks are generated at the edge of the well, and no cracks are generated in the portion to be used for microscopic observation.

Incidentally, the antibacterial agent-introduced plate containing the dried antimicrobial-containing culture medium is described as a final product form in the present embodiment, but a transparent plate made of a resin that includes the above-described trap portion, at a stage before introducing the antibacterial agent, may be used as a final product form.

Hereinafter, various working examples according to the embodiment of the present disclosure will be described with reference to the accompanying drawings. However, these working examples are merely examples for realizing the present disclosure, and do not limit the technical scope of the present disclosure. Further, the same reference numerals are assigned to the common configurations in the respective drawings.

(2) Working Example 1

Configuration Example of Culture Instrument

FIGS. 1A-1D are views for describing a configuration of an antibacterial agent-introduced plate 11 according to Working Example 1. The antibacterial agent-introduced plate 11 is configured to include a plurality of wells 14 (for example, configured to include a total of 96 wells 14 in 12 columns×8 rows). FIG. 1A is a perspective view illustrating the antibacterial agent-introduced plate 11 and some of the enlarged wells 14.

The antibacterial agent-introduced plate 11 includes the plurality of wells 14 each having an open top. The well 14 contains a culture medium, a culture medium containing an antibacterial agent, or the like. As illustrated in FIG. 1A, the antibacterial agent-introduced plate 11 includes, for example, a total of 96 wells 14 arranged in 12 columns×8 rows.

Figure 1B:
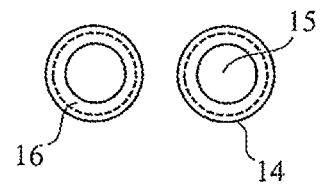

FIG. 1B is a view illustrating a state of upper surfaces of some of the wells 14 of the antibacterial agent-introduced plate 11. In the example illustrated in FIG. 1B, a microscopic observation portion 15 is arranged so as to be located at the center of a bottom surface of the well 14, and a recess 16 whose height is lower than the microscopic observation portion 15 is arranged so as to be located around the microscopic observation portion 15. The recess 16 is located near a bottom surface of an inner wall of the well 14. Incidentally, the recess 16 is formed over the entire circumference of the inner wall in FIG. 1C, but it is sufficient to form the recess 16 at least a part of the circumference instead of the entire circumference.

Figure 1C:
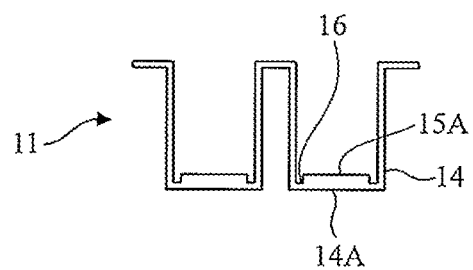

FIG. 1C is a side cross-sectional view of the plurality of wells 14. As illustrated in FIG. 1C, the microscopic observation portion 15 arranged in the well 14 is arranged so as to be one step higher than the recess 16 arranged near the side wall of the well, and the microscopic observation portion 15 has a surface 15A that is substantially parallel to a bottom surface 14A of the well 14.

Figure 1D:
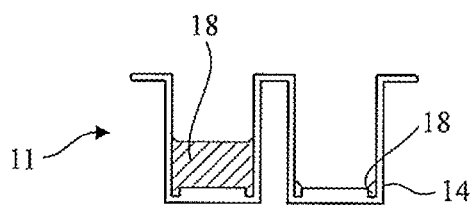

As illustrated in FIG. 1D, the recess 16 is designed such that a small amount of liquid 18 would remain in the recess 16 due to a meniscus when the liquid 18 has been introduced into the well 14. For example, the width of the recess 16 may be about 1 mm or less (preferably about 0.5 mm or less), and a depth thereof is designed to be about 1 mm or less (preferably about 0.5 mm or less). FIG. 1D illustrates a state where the left well 14 is filled with the liquid 18 by about half of the well. In this case, both the microscopic observation portion 15 and the recess 16 are in contact with the liquid 18. On the other hand, the right well 14 is in a state where a small amount of liquid is introduced in the well. In this case, the liquid 18 is not in contact with the liquid 18 but is in contact with the recess 16 since the height of the surface of the microscopic observation portion 15 is higher than that of the well bottom surface 14A.

When the antibacterial agent-introduced plate is prepared, the preparation is performed by introducing the culture medium containing the antibacterial agent into the well, and then, performing vacuum drying of the liquid introduced into the well. When a condition for the vacuum drying is severe (when the degree of vacuum is higher than a predetermined value), cracks are sometimes generated on the bottom surface of the resin plate when the liquid in the well evaporates. This is because the bottom surface of the resin plate is damaged when the liquid evaporates. If the condition for the vacuum drying is mild (when the degree of vacuum is equal to or less than the predetermined value), the liquid gradually evaporates, and thus, the liquid evaporates from the recess 16. Thus, even if cracks are generated, the generation point is only limited to the vicinity of the recess 16, that is, near the side wall of the well. Since the liquid under the microscopic observation portion 15 arranged near the center of the well 14 moves toward the recess 16 due to the meniscus, the bottom surface 15A of the microscopic observation portion is not damaged. As a result, the antibacterial agent-introduced plate having the microscopic observation portion 15 having no cracks can be obtained.

Some conventional antibacterial agent-introduced plates have cracks on a bottom surface of a well, but these cracks are small cracks that are hardly confirmed with the naked eye. Thus, there is no influence on the turbidity measurement. Since the antibacterial agent-introduced plate of the present disclosure can provide the plate having no cracks in the microscopic observation portion, it is a matter of course that there is no adverse effect on the microscopic observation, and there is no influence even on the conventional turbidity measurement.

In the antibacterial agent-introduced plate 11 of the present disclosure, at least the bottom surface 14A portion of the well 14 and the microscopic observation portion 15 of the antibacterial agent-introduced plate 11 are made of a material having a light-transmitting property (light transparency) in order to implement desired optical measurement. Examples of the light-transmitting material used for the antibacterial agent-introduced plate 11 and the microscopic observation portion 15 of the present disclosure include polypropylene, polystyrene, and polycarbonate.

<Configuration of Optical System for Microscopic Observation>

Figure 2:
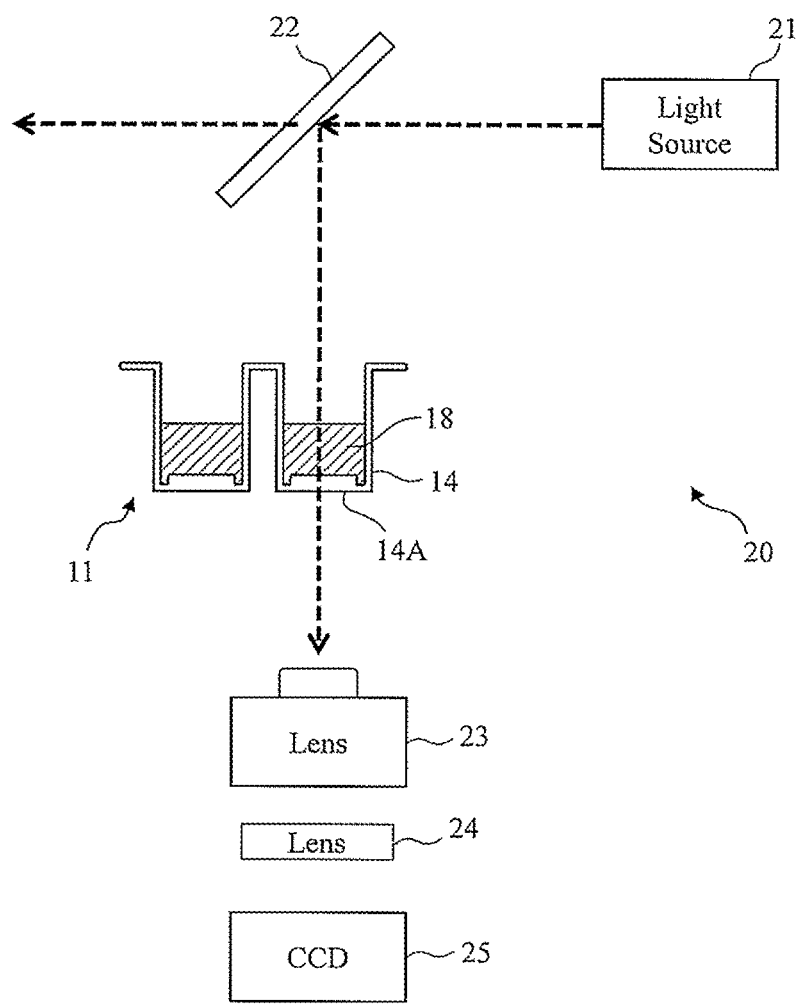
FIG. 2 is a diagram illustrating a configuration example of an optical system for microscopic observation.

FIG. 2 is a diagram for describing an optical system 20 for the turbidity measurement. The optical system 20 includes a light source 21, a dichroic mirror 22, an objective lens 23, an imaging lens 24, and a CCD 25.

A part of light emitted from the light source 21 passes through the dichroic mirror 22, and the rest thereof is reflected by the dichroic mirror 22. The light reflected by the dichroic mirror 22 passes through the well 14, the liquid 18, and the bottom surface 14A of the well 14, and is detected by the CCD 25 through the objective lens 23 and the imaging lens 24. Incidentally, the dichroic mirror 22 may be a half mirror in the optical system 20.

<Modification>

Although the antibacterial agent-introduced plate 11 is provided with the 96 wells 14 in the configuration example of Working Example 1 (FIGS. 1A-1D), the number of the wells 14 provided in the antibacterial agent-introduced plate 11 is not limited to the above value. The antibacterial agent-introduced plate 11 can have the arbitrary number of wells 14.

Figure 3:
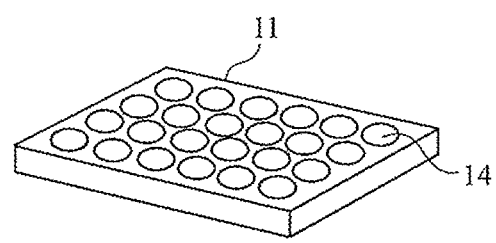
FIG. 3 is a view illustrating the antibacterial agent-introduced plate including a total of 24 wells as an example.

FIG. 3 is a view illustrating a configuration example of the antibacterial agent-introduced plate 11 including a total of 24 containers (wells) 14. In the example illustrated in FIG. 3, the 24 wells 14 are arranged in 6 columns×4 rows. When the antibacterial agent-introduced plate 11 includes the plurality of wells 14 as described above, antimicrobial susceptibility testing can be simultaneously performed under different conditions.

Figure 4:
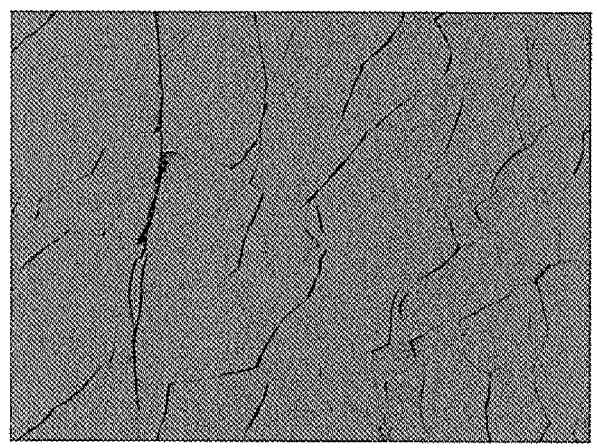
FIG. 4 is a view illustrating a state of cracks on a plate bottom surface (Comparative Example).
Figure 5:
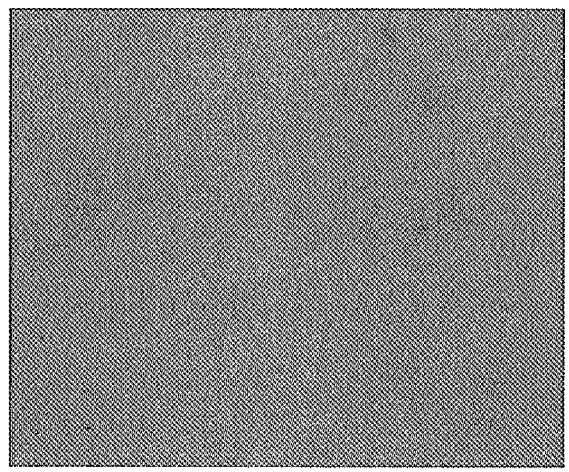
FIG. 5 is a view illustrating a state of a plate bottom surface having no cracks (Working Example 1).

FIG. 4 is a view illustrating an image (example) obtained when a plate used in the conventional antimicrobial susceptibility testing is observed with a microscope using the optical system illustrated in FIG. 2. It can be understood that cracks were observed in the state of not including bacteria. On the other hand, FIG. 5 is a view illustrating an image (example) obtained when the antibacterial agent-introduced plate 11 according to Working Example 1 is observed with a microscope having the optical system illustrated in FIG. 2. As illustrated in FIG. 5, it can be understood that no cracks were generated in the microscopic observation portion 15.

(3) Working Example 2

In the antibacterial agent-introduced plate 11 of Working Example 1, the well 14 has a straight shape. On the other hand, the antibacterial agent-introduced plate 11 of Working Example 2 may have a shape in which a side wall of the well 14 is tapered. In recent years, a container (well) having a tapered shape is often used. This is because a culture medium can be collected in the middle (microscopic observation portion 15) of the container (well) even if the degree of growth of bacteria or fungi in a culture medium is relatively low, and it becomes possible to efficiently perform the growth determination. The technical concept of the present disclosure can be applied to such a well having a tapered shape.

Figure 6A:
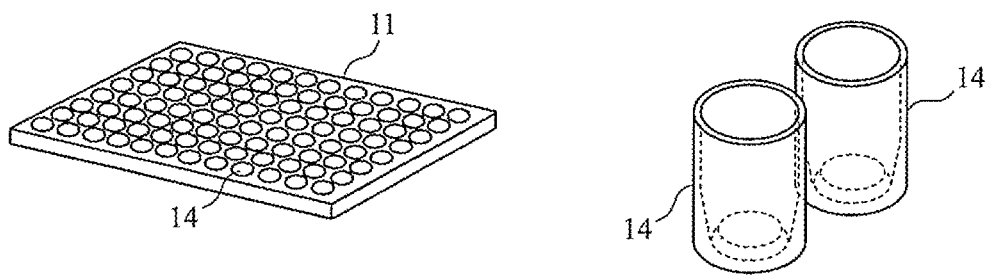
FIGS. 6A-6D are views illustrating a configuration example of an antibacterial agent-introduced plate according to Working Example 2.

FIGS. 6A-6D are views illustrating a configuration example of the antibacterial agent-introduced plate 11 according to Working Example 2. The antibacterial agent-introduced plate 11 is configured to include a plurality of wells 14 (for example, configured to include a total of 96 wells 14 in 12 columns×8 rows). FIG. 6A is a perspective view illustrating the antibacterial agent-introduced plate 11 and some of the enlarged wells 14.

The antibacterial agent-introduced plate 11 includes the plurality of wells 14 each having an open top. The well 14 contains a culture medium, a culture medium containing an antibacterial agent, or the like. In the example illustrated in FIG. 6A, the antibacterial agent-introduced plate 11 has a total of 96 wells 14 arranged in 12 columns×8 rows.

Figure 6B:
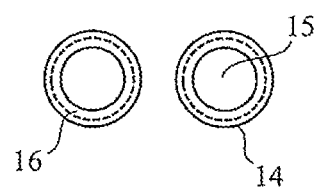

FIG. 6B is a view illustrating a shape of upper surfaces of some of the wells 14 of the antibacterial agent-introduced plate 11. In the example illustrated in FIG. 6B, the microscopic observation portion 15 is arranged so as to be located at the center of a bottom surface of the well 14, and the recess 16 whose height is lower than the microscopic observation portion 15 is arranged so as to be located around the microscopic observation portion 15. The recess 16 is located near a bottom surface of an inner wall of the well 14.

Figure 6C:
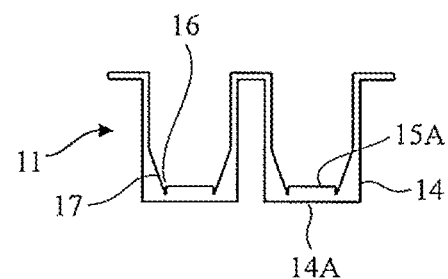

FIG. 6C is a side cross-sectional view of the plurality of wells 14. As illustrated in FIG. 6C, the microscopic observation portion 15 arranged in the well 14 is provided so as to be one step higher than the recess 16 arranged near the side wall of the well, and has the surface 15A that is substantially parallel to the bottom surface 14A of the well 14. Further, a tapered portion 17 is provided on the side wall of the well 14.

Figure 6D:
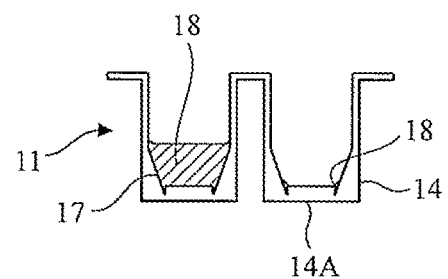

As illustrated in FIG. 6D, the recess 16 is designed such that a small amount of liquid 18 would remain in the recess 16 due to a meniscus when the liquid 18 has been introduced into the well 14. A width of the recess 16 may be about 1.0 mm or less (preferably about 0.5 mm or less), and a depth thereof is designed to be about 1.0 mm or less (preferably about 0.5 mm or less). In FIG. 6D, the left well 14 is in a state where the liquid 18 is filled by about half of the well. In this case, both the microscopic observation portion 15 and the recess 16 are in contact with the liquid 18. On the other hand, the right well 14 is in a state where a small amount of liquid is introduced in the well. In this case, the microscopic observation portion 15 is not contact with the liquid 18, but the liquid 18 is in contact with the recess 16, since the height of the microscopic observation portion 15 is higher than that of the recess 16 with respect to the well bottom surface 14A.

Materials of the antibacterial agent-introduced plate 11 and the microscopic observation portion 15 can be selected from the same materials as the materials of the antibacterial agent-introduced plate 11 and the microscopic observation portion 15 described in Working Example 1.

Figure 7:
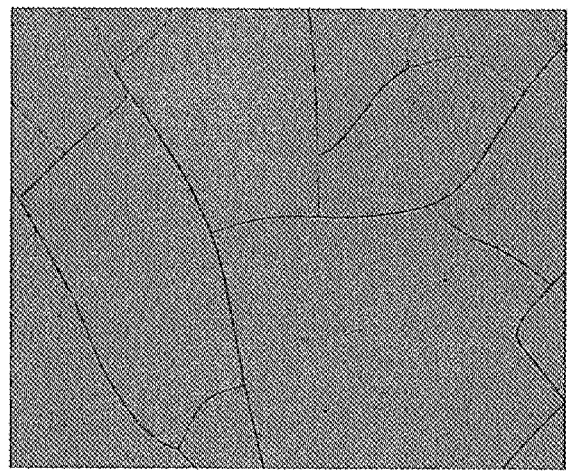
FIG. 7 is a view illustrating a state of cracks on a plate bottom surface (Comparative Example).
Figure 8:
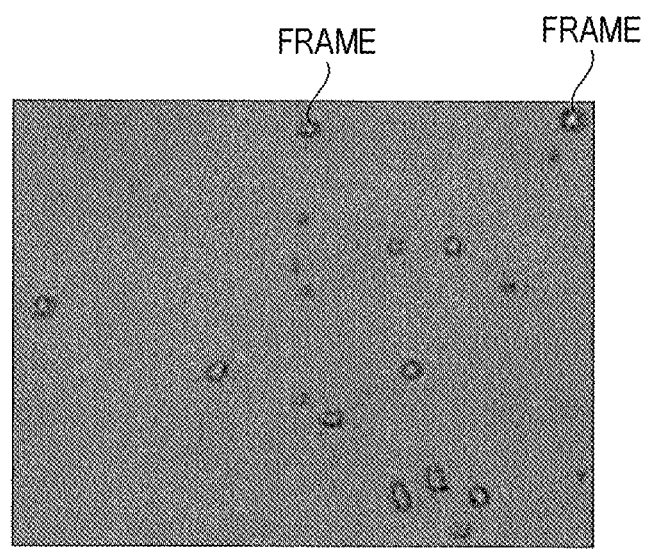
FIG. 8 is a view illustrating a state of a plate bottom surface having no cracks (Working Example 2).

FIG. 7 illustrates an image obtained by microscopic observation of a plate having a tapered well used in the conventional antimicrobial susceptibility testing using the optical system illustrated in FIG. 2. It can be understood that cracks were observed in the state of not including bacteria. On the other hand, FIG. 8 illustrates an image obtained by microscopic observation of the antibacterial agent-introduced plate 11 having the tapered well according to the present disclosure using the optical system illustrated in FIG. 2. It can be understood that no cracks were generated in the microscopic observation portion, and bacteria (portions surrounded by frames in FIG. 8: only some of the bacteria are indicated by the "frames" in FIG. 8) could be detected.

(4) Working Example 3

In the antibacterial agent-introduced plate 11 of Working Example 1, the wells 14 is provided with the recess at the edge. On the other hand, in the antibacterial agent-introduced plate 11 of Working Example 3, a protrusion is provided on a bottom surface of the well 14.

Figure 9A:
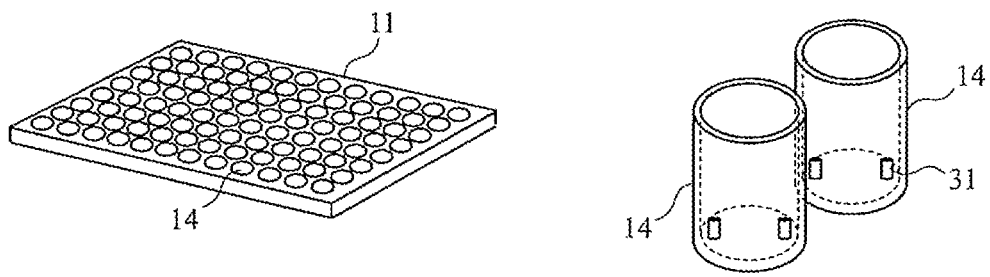
FIGS. 9A-9D are views illustrating a configuration example of an antibacterial agent-introduced plate according to Working Example 3.

FIGS. 9A-9D are views for describing configurations of the antibacterial agent-introduced plate 11 according to Working Example 3. The antibacterial agent-introduced plate 11 is configured to include a plurality of wells 14 (for example, configured to include a total of 96 wells 14 in 12 columns×8 rows). FIG. 9A is a perspective view illustrating the antibacterial agent-introduced plate 11 and some of the enlarged wells 14.

The antibacterial agent-introduced plate 11 includes the plurality of wells 14 each having an open top. The well 14 contains a culture medium, a culture medium containing an antibacterial agent, or the like. In the example illustrated in FIG. 9A, the antibacterial agent-introduced plate 11 has a total of 96 wells 14 arranged in 12 columns×8 rows.

Figure 9B:
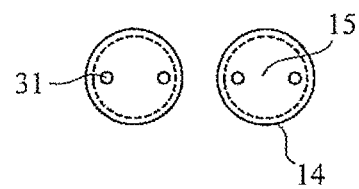

FIG. 9B is a view illustrating a shape of upper surfaces of some of the wells 14 of the antibacterial agent-introduced plate 11. In the example illustrated in FIG. 9B, the microscopic observation portion 15 is arranged so as to be located at the center of a bottom surface of the well 14, and protrusions 31 each having a higher height than the microscopic observation portion 15 are arranged so as to be located around the microscopic observation portion 15. The protrusion 31 is located near a side wall of an inner wall of the well 14.

Figure 9C:
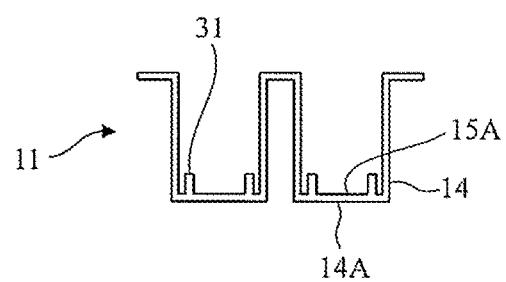

FIG. 9C is a side cross-sectional view of the plurality of wells 14. As illustrated in FIG. 9C, the protrusion 31 arranged in the well 14 is provided so as to be one step higher than the microscopic observation portion 15 arranged at the center of the well.

Figure 9D:
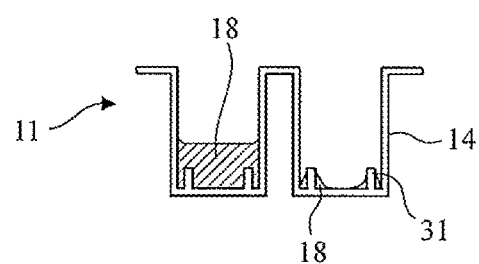

As illustrated in FIG. 9D, the protrusion 31 is designed such that a small amount of liquid 18 would be trapped by the protrusion 31 due to surface tension when the liquid 18 has been introduced into the well 14. A width of the protrusion may be, for example, about 1.0 mm or less (preferably, about 0.5 mm or less), and a height thereof is designed to be about 1.0 mm or less (preferably, about 0.5 mm or less). Although two protrusions 31 are provided in FIGS. 9A-9D, at least one protrusion 31 may be provided.

In FIG. 9D, the left well 14 is in a state where the liquid 18 is filled by about half of the well. In this case, both the microscopic observation portion 15 and the protrusion 31 are in contact with the liquid 18. On the other hand, the right well 14 is in a state where a small amount of liquid is introduced in the well. In this case, since the liquid 18 is trapped by the protrusion 31, a portion that is not in contact with the liquid 18 is formed in the microscopic observation portion 15. As a result, the antibacterial agent-introduced plate having no cracks can be prepared.

Materials of the antibacterial agent-introduced plate 11 and the microscopic observation portion 15 can be selected from the same materials as the materials of the antibacterial agent-introduced plate 11 and the microscopic observation portion 15 described in Working Example 1.

(5) Working Example 4

In the antibacterial agent-introduced plate 11 of Working Example 3, the protrusion is provided on the bottom surface of the well 14 (a space is present between the inner wall of the well 14 and the protrusion). On the other hand, as in Working Example 4, a protrusion is provided on a side surface of the well 14 (the protrusion is in contact with an inner wall of the well 14, or the protrusion is integrated with the inner wall of the well 14).

Figure 10A:
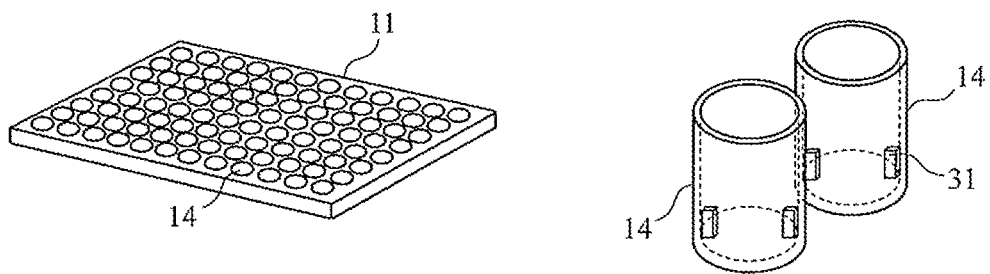
FIGS. 10A-10D are views illustrating a configuration example of an antibacterial agent-introduced plate according to Working Example 4.

FIGS. 10A-10D are views illustrating a configuration example of the antibacterial agent-introduced plate 11 according to Working Example 4. The antibacterial agent-introduced plate 11 is configured to include a plurality of wells 14 (for example, configured to include a total of 96 wells 14 in 12 columns×8 rows). FIG. 10A is a perspective view illustrating the antibacterial agent-introduced plate 11 and some of the enlarged wells 14.

The antibacterial agent-introduced plate 11 includes the plurality of wells 14 each having an open top. The well 14 contains a culture medium, a culture medium containing an antibacterial agent, or the like. In the example illustrated in FIG. 10A, the antibacterial agent-introduced plate 11 has a total of 96 wells 14 arranged in 12 columns×8 rows.

Figure 10B:
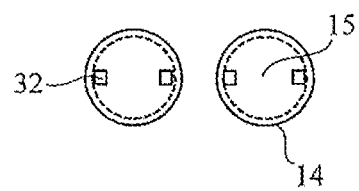

FIG. 10B is a view illustrating a shape of upper surfaces of some of the wells 14 of the antibacterial agent-introduced plate 11. In the example illustrated in FIG. 10B, the microscopic observation portion 15 is arranged so as to be located at the center of a bottom surface of the well 14, and protrusions 32 each having a higher height than the microscopic observation portion 15 are arranged so as to be in contact with the side surface of the well.

Figure 10C:
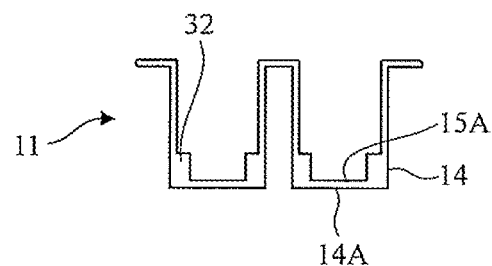

FIG. 10C is a side cross-sectional view of the plurality of wells 14. As illustrated in FIG. 10C, the protrusion 32 arranged on the side surface of the well 14 is provided so as to be one step higher than the microscopic observation portion 15 arranged at the center of the well.

Figure 10D:
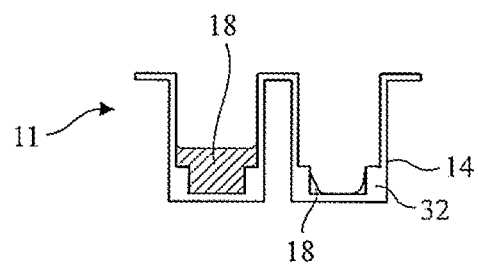

As illustrated in FIG. 10D, the protrusion 32 is designed such that a small amount of liquid 18 would be trapped by the protrusion 32 due to surface tension when the liquid 18 has been introduced into the well 14. A width of the protrusion may be about 1.0 mm or less (preferably, about 0.5 mm or less), and a height thereof is designed to be about 1.0 mm or less (preferably, about 0.5 mm or less). The left well 14 in FIG. 10D illustrates a state of being filled with the liquid 18 by about half of the well. In this case, both the microscopic observation portion 15 and the protrusion 32 are in contact with the liquid 18. On the other hand, the right well 14 illustrates a state where a small amount of liquid is introduced in the well. In this case, since the liquid 18 is trapped by the protrusion 32, a portion that is not in contact with the liquid 18 is formed in the microscopic observation portion 15. As a result, the antibacterial agent-introduced plate having no cracks can be prepared.

Materials of the antibacterial agent-introduced plate 11 and the microscopic observation portion 15 can be selected from the same materials as the materials of the antibacterial agent-introduced plate 11 and the microscopic observation portion 15 described in Working Example 1.

(6) Summary

An antibacterial agent-introduced plate according to the present embodiment includes a plurality of holding portions (wells) that hold a culture medium used for antimicrobial susceptibility testing, and the plurality of holding portions hold a dried culture medium and antibacterial agent. Here, the bottom surface of each of the wells has a light-transmitting surface, and the trap portion that traps the culture medium (traps the culture medium in the step of drying the culture medium under vacuum) is provided on a part of the bottom surface. The trap portion is a recess provided at the edge of the bottom surface, a protrusion formed on a part of the bottom surface, or the protrusion provided on a side wall of the well (integrated with the side wall). In this manner, in the culture medium vacuum drying step, the culture medium can be held in the trap portion such that the culture medium does not touch a microscopic observation surface, and thus, it is possible to prevent the microscopic observation surface from cracking. Incidentally, regarding the trap portion (the recess, the protrusion, or the like), the well and the trap portion can be integrally molded by forming a portion corresponding to the trap portion in a mold for manufacturing a well and pouring and solidifying resin in the mold.

When the antibacterial agent-introduced plate provided with the plate bottom surface having no cracks is used as described above, it is possible to observe bacteria by a microscope with high accuracy. The antibacterial agent-introduced plate is supplied to a user in a state where a culture medium containing various types of antibacterial agents at various concentrations has been introduced in advance and dried under vacuum. The supply in the dried state enables distribution and storage at room temperature, and a state that can be used for antimicrobial susceptibility testing is realized simply by introducing water into the well for redissolving, and thus, user's operation during the testing can be simplified.

Incidentally, the present disclosure is not limited to the above-described working examples and includes various modifications. For example, the above-described working examples have been described in detail in order to describe the present disclosure in an easily understandable manner, and are not necessarily limited to one including the entire configuration that has been described above. Further, some configurations of a certain working example can be replaced by configurations of another working example, and further, a configuration of another working example can be also added to a configuration of a certain working example. Further, addition, deletion or substitution of other configurations can be made with respect to some configurations of each working example.

REFERENCE SIGNS LIST 11 antibacterial agent-introduced plate
14 well
15 microscopic observation portion
16 recess
17 tapered portion
18 liquid
20 optical system
21 light source
22 dichroic mirror
23 objective lens
24 imaging lens
25 CCD
31, 32 protrusion

The invention claimed is:

1. An antibacterial agent-introduced plate comprising a plurality of holding portions configured to hold a culture medium used for antimicrobial susceptibility testing, the plurality of holding portions holding dried culture medium and antibacterial agent, wherein
   a bottom surface of each of the plurality of holding portions includes a light-transmitting surface,
   each of the plurality of holding portions includes a trap portion that traps the culture medium on an edge of the bottom surface, and the trap portion holding a liquid,
   the bottom surface includes the antibacterial agent that is introduced when the antibacterial agent-introduced plate is prepared,
   a plurality of wells corresponding to the plurality of holding portions respectively hold different types of antibacterial agents at different concentrations,
   a microscopic observation portion located at a center of the bottom surface of each of the plurality of holding portions, and
   each of the plurality of holding portions including at least one of a meniscus or surface tension of the liquid preventing the liquid from being in contact with the microscopic observation portion.

2. The antibacterial agent-introduced plate according to claim 1, wherein the trap portion is a recess formed on a part of the bottom surface.

3. The antibacterial agent-introduced plate according to claim 2, wherein a width of the recess is 0.5 mm or less, and a depth of the recess is 0.5 mm or less.

4. The antibacterial agent-introduced plate according to claim 1, wherein each side wall of the plurality of holding portions has a tapered shape.

5. The antibacterial agent-introduced plate according to claim 1, wherein the trap portion is a protrusion formed on a part of the bottom surface.

6. The antibacterial agent-introduced plate according to claim 1, wherein the trap portion is a protrusion provided on a side wall of the holding portion.

7. A transparent plate comprising a plurality of wells, wherein
each of the plurality of wells includes a light-transmitting bottom surface and a side wall,
each of the plurality of wells includes a trap portion that traps a predetermined liquid on an edge of the bottom surface, and the trap portion holding a liquid,
the bottom surface includes an antibacterial agent that is introduced when the transparent plate is prepared,
each of the plurality of wells respectively hold different types of antibacterial agents at different concentrations,
a microscopic observation portion located at a center of the bottom surface of each of the plurality of wells, and
each of the plurality of wells include at least one of a meniscus or surface tension of the liquid preventing the liquid from being in contact with the microscopic observation portion.

8. The transparent plate according to claim 7, wherein the side wall has a tapered shape.

9. The transparent plate according to claim 7, wherein the trap portion is a protrusion formed on an edge of the bottom surface.

10. The transparent plate according to claim 7, wherein the trap portion is a protrusion provided on the side wall.

* * * * *